United States Patent [19]

Blanchard

[11] Patent Number: 5,203,791
[45] Date of Patent: Apr. 20, 1993

[54] DEVICE FOR ATTACHING A PROSTHESIS

[76] Inventor: J. Wayne Blanchard, 60320 Lafourche St., Plaquemine, La. 70764

[21] Appl. No.: 893,797

[22] Filed: Jun. 4, 1992

[51] Int. Cl.$^5$ .............................................. A61F 2/48
[52] U.S. Cl. ....................................... 623/24; 623/27; 623/33; 623/34
[58] Field of Search ................... 623/27, 33, 34, 38, 623/24, 25

[56] References Cited

U.S. PATENT DOCUMENTS

| 2,666,927 | 1/1984 | Morheijer | 623/27 |
| 3,922,727 | 12/1975 | Bianco | 623/24 |
| 4,221,007 | 9/1980 | Wilson | 623/38 |
| 4,923,476 | 5/1990 | Cooper et al. | 623/38 |

FOREIGN PATENT DOCUMENTS

2027212 1/1971 Fed. Rep. of Germany ........ 623/27

Primary Examiner—Ronald Frinks
Attorney, Agent, or Firm—Reginald F. Roberts, Jr

[57] ABSTRACT

A device for attaching a prosthesis to an above-the-knee amputee. The device includes a frame which is vertically adjustable for different working heights. A motor is mounted on the frame, and is controlled by a switch. One end of a shaft is connected to the motor, which turns the shaft. The other end of the shaft is disposed in a bearing supported by the frame. A clip holds one end of a tubular stocking in contact with the shaft. As the shaft turns, the stocking is wrapped around the shaft, drawing the stocking toward the shaft.

17 Claims, 8 Drawing Sheets

DEVICE FOR ATTACHING A PROSTHESIS

BACKGROUND OF THE INVENTION

The present invention relates to a device for attaching a prosthesis to an amputee. More particularly, the invention relates to a machine for attaching an artificial leg to an above-the-knee (AK) amputee.

There is almost always some degree of difficulty and discomfort experienced by AK amputees in attaching an artificial leg to the stump of the amputee's limb. The degree of difficulty is extreme when the amputee is otherwise physically disabled or handicapped; e.g., a double amputee having an amputation of a leg and an arm.

The usual manner of attaching an artificial leg to the stump of an AK limb is as follows. The amputee pulls a tubular stocking over the stump of the limb, using one end of the stocking. The amputee then places the other end of the stocking into the valve housing of the socket of the artificial limb. The amputee next uses a slightly upward motion of the hip to allow the fatty tissue of the stump to be pulled down into the socket; then pulls the stocking completely out of the socket. Finally, the amputee places the valve inside the housing to form suction on the socket, thereby attaching the prosthesis to the stump.

Since all of the above steps are characterized by some degree of difficulty, particularly with an otherwise-disabled amputee, the necessary combination of steps is unduly difficult and troublesome for such individuals. There is therefore a pressing need for a device which can assist the AK amputee in attaching the prosthesis. The present invention provides such a device.

SUMMARY OF THE INVENTION

In general, the present invention provides a machine for attaching a prosthesis to an above-the-knee (AK) amputee. The machine comprises a frame which is vertically adjustable for different working heights or elevations. A motor is mounted on the frame, and is controlled by means for turning the motor on and off. A rigid elongated horizontal member having first and second ends is rotatably connected to the motor. The first end of the elongated member is connected to the motor, which drives and turns the elongated member, and the second end of the elongated member is rotatably disposed in a bearing which is supported by the frame. Means are provided for holding the first end of a tubular stocking having first and second ends in contact with the elongated member. The elongated member and the holding means are constructed and arranged so that, as the elongated member is turned by the motor, the tubular stocking is wrapped around the elongated member, thereby drawing the second end of the stocking toward the shaft.

DETAILED DESCRIPTION OF THE INVENTION

More specifically, reference is made to FIGS. 1-5, in which is shown a first embodiment of a prosthetic machine made in accordance with the principles of the present invention, and generally designated by the numeral 2.

The machine 2 comprises a horizontal base 4 having a first end 4a, a second end 4b, a first side 4c, and a second side 4d. The first end 4a is herein designated the front end, the second end 4b the rear end, the first side 4c the right-hand side, and the second side 4b the left-hand side.

First, second, and third stationary vertical support members 34, 36, and 38, respectively, are fastened to the base 4. Disposed within the first, second, and third support members 34, 36, and 38 are first, second, and third movable vertical support members 34a, 36a, and 38a, respectively. Both the stationary and the movable support members are perforated, to provide openings 35 therein which are alignable with one another between the stationary and movable support members. The heights of the movable support members 34a, 36a, and 38a are determined and adjusted by disposing pins 28 in the aligned openings 35 of the stationary and movable support members, and by holding said pins in position by means of set-screws 39. The pins 28 are beneficially provided with rings 30 attached thereto, to facilitate manipulation of the pins.

A horizontal plate 15 is supported by the first and second movable support members 32a and 34a. In turn, the plate 15 supports a motor 12 disposed in a housing 12a, and a vertical plate 16 in which is disposed one end 14c of a shaft 14 turnable by the motor 12. The shaft 14 comprises a first end 14a, which is connected to the motor; an enlarged portion 14b to which is fastened a horizontal clip 40; and a second end 14c which is disposed in and supported by the vertical plate 16. To the face of the plate 16 facing away from the motor 12 is attached a pillow block bearing 18. The end 14c of the shaft 14 passes through an opening in the plate 16, and is disposed in the bearing 18. The plate 16 thus functions as a motor mount.

The horizontal plate 15 comprises first and second ends 15a, 15c, and an indented, recessed, or concave portion 15b connecting the ends 15a, 15c. The indented portion 15b effectively braces the prosthesis and thereby prevents the prosthesis from buckling at the knee. The first end 15a of the plate 15 is supported by the first movable support member 32a. The second end 15c of the plate 15 is supported by the second movable support member 34a.

The third stationary support member 36 is connected to the second stationary support member 34 by a brace 31. Connected to the upper end of the movable support member 36a is a horizontal bar 6 which serves as a handlebar. Below the handlebar 6 a control panel 10 is connected to the upper end of the movable support member 36a by a bracket 8. The control panel 10 is provided with a switch 10a for starting and stopping the motor 12. The switch 10a is a momentary switch which can be started and stopped at any time.

The motor 12 is a reversible electric gear motor which has a pulling torque of seventy-six inch-pounds. The speed of the motor 12 is 8.8 revolutions per minute (rpm), with an overhang torque of ninety inch-pounds.

The handlebar 6 is held manually for balance by an amputee using the device 2. Since the motor 12 is reversible, the handlebar 6 and the machine 2 can be used by an amputee missing part of either the right or the left leg, or of both legs.

The height of the shaft 14 is from about fourteen to about twenty-eight inches above the base 4. The height of the handlebar 6 is either about twenty-two or about thirty-six inches above the base 4.

The frame, which comprises the plates 15 and 16, stationary support members 32, 34, and 36, and movable support members 32a, 34a, and 36a, is preferably made of aluminum. The pillow block bearing 18 is preferably made of a plastic material. Even more preferably, the bearing 18 is made of a plastic polymer or resin marketed under the trademark DELRIN (a polyformaldahyde of greater than 15,000 molecular weight sold by DuPont).

The motor 12 and control panel 10 are connected to one another and to an electrical outlet (not shown) by electrical cords 24 and 26. The electrical outlet is a 110-120 volt alternating-current outlet.

Figure 6:
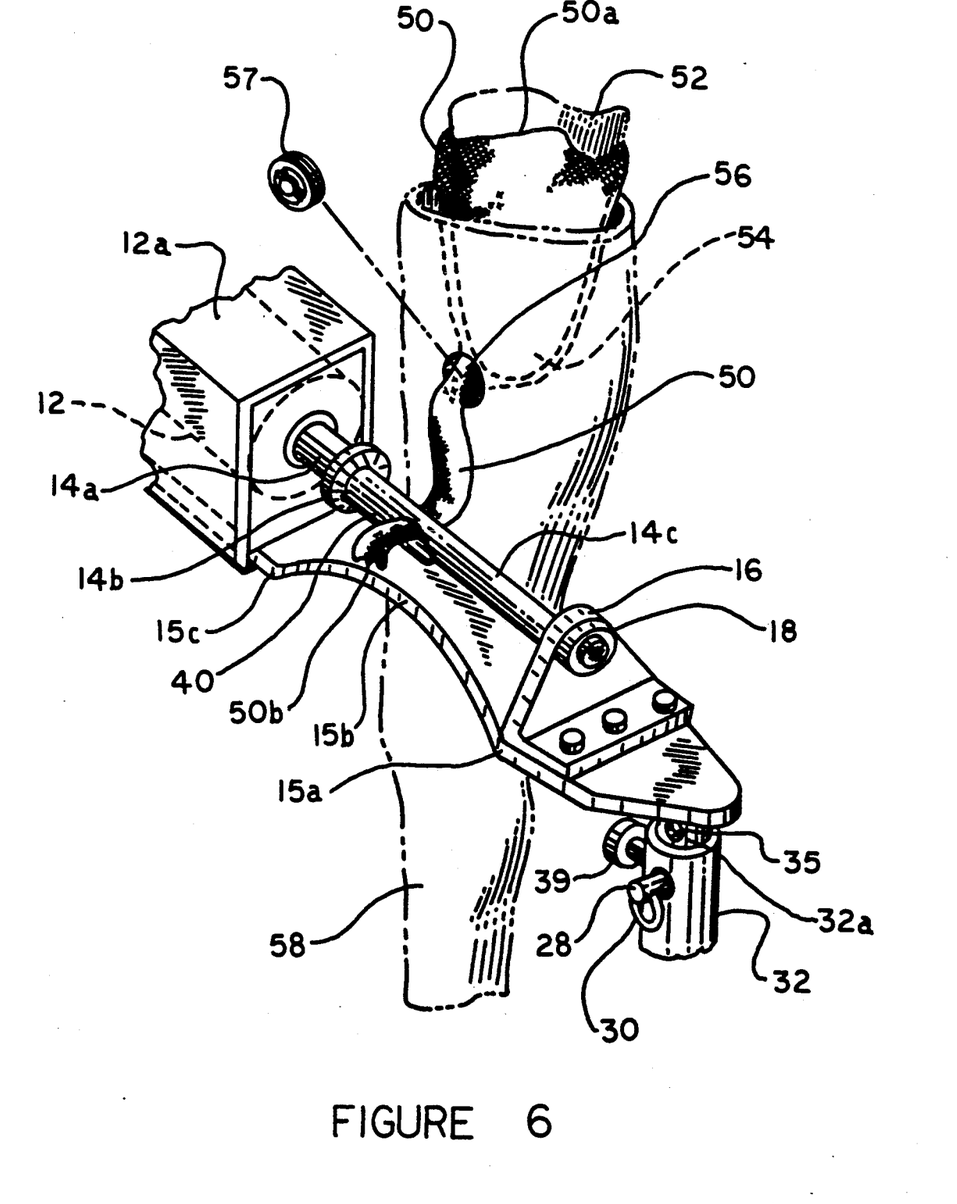
FIG. 6 is an isometric and partially-exploded view of a portion of the machine shown in FIG. 1, illustrating the use of the machine.

Reference is now made to FIG. 6, in which is illustrated the use of the prosthetic machine 2. To use the device 2, an amputee first pulls a tubular stocking 50 up over the stump 52 of the leg (not shown), using one end 50a of the stocking 50. The amputee removes the valve 57 from the valve housing 56 of the socket 54 of the artificial limb 58. The amputee then places the other end 50b of the hollow stocking into the valve housing 56 of the socket 54 of the artificial limb 58, while holding the valve 57. The amputee next disposes the other end of the stocking 50b between the rotatable shaft 14 and the clip 40, where the stocking 50 is held, while straddling the horizontal plate 15 with the legs at the indented portion 15b, facing to the rear, and grasping the handlebar 6. The motor 12 is then turned on, using the switch 10a; and then, while the amputee uses a slightly upward motion of the hip to allow the fatty tissue of the stump 52 to be pulled down into the socket 54, the stocking 50 is pulled completely out of the socket 54 as the motor 12 winds the stocking 50 around the rotating shaft 14. After the stocking 50 has been pulled out of the socket 54, the amputee replaces the valve 57 inside the valve housing 56 to form suction on the socket 54, thereby attaching the prosthesis 58 to the stump 52.

Figure 7:
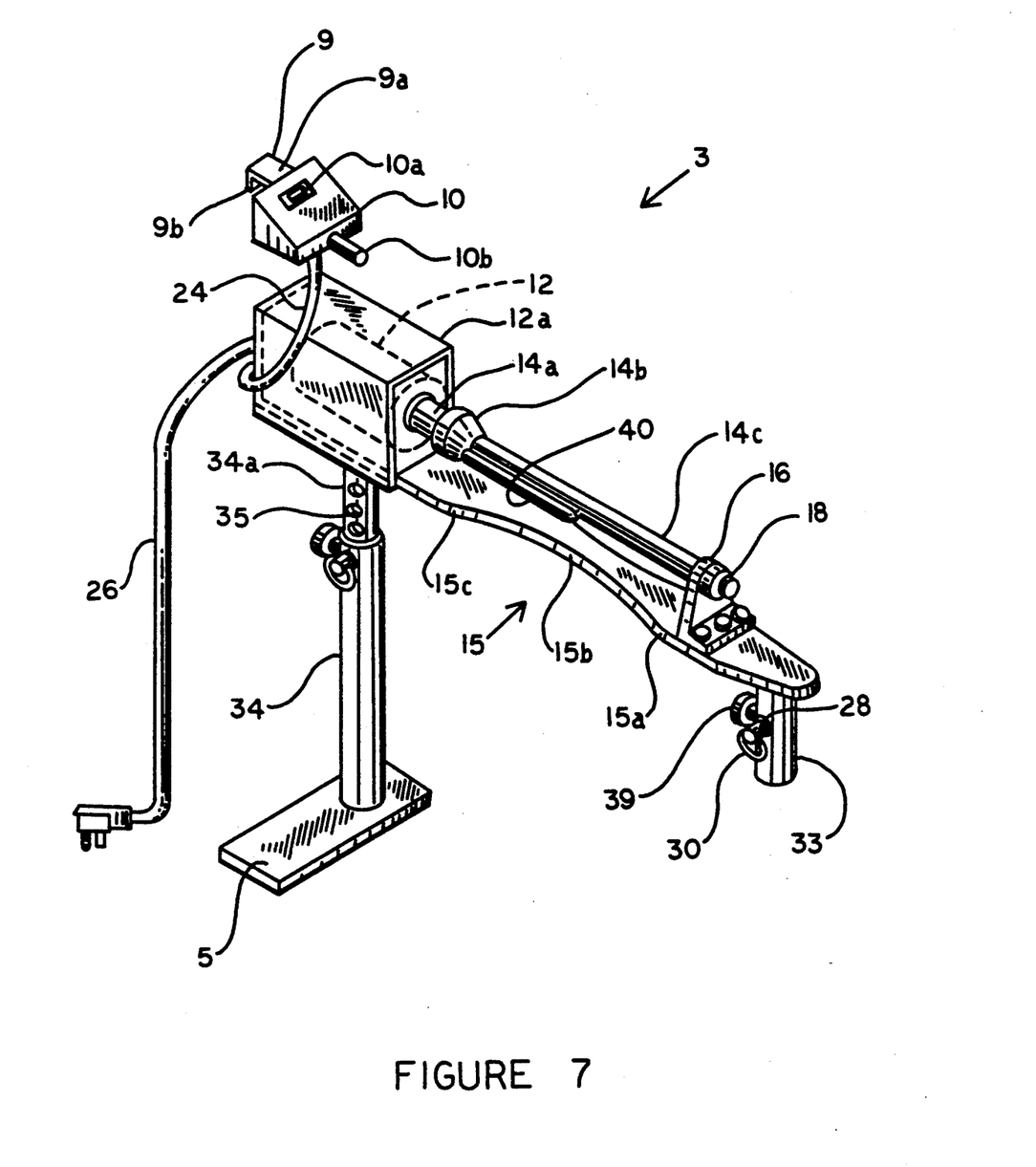
FIG. 7 is an isometric view of a second embodiment of a prosthetic machine made in accordance with the principles of the present invention.

Reference is now made to FIG. 7, wherein is shown a second and portable embodiment of a prosthetic machine made in accordance with the principles of the present invention, and generally designated by the numeral 3.

The machine 3 comprises a horizontal base 5 to which is fastened a first stationary support member 34 in which is disposed a first movable support member 34a. A horizontal plate 15 is supported by the movable support member 34a and by a second stationary support member 33. The second support member 33 is similar to the stationary support member 32 of the first embodiment 2 of the machine shown in FIG. 4, but is shorter than the support member 32. The support member 33 is fastened to the lower surface of the plate 15.

The control panel 10 is movable in this second embodiment 3, and is constructed and arranged to be held by the amputee, using as a handle a horizontal bar 10b attached to the control panel 10. Also attached to the panel 10 is an L-shaped member 9 having a horizontal portion 9a and a downwardly-directed vertical portion 9b.

The remainder of the machine 3 is similar to the machine 2. The machine 3, however, is portable. It can be beneficially transformed into a fixed machine similar to the machine 2 by removing the base 5 and stationary support member 34, and mounting the remainder of the machine 3 on a frame 5 shown in FIG. 8.

Figure 1:
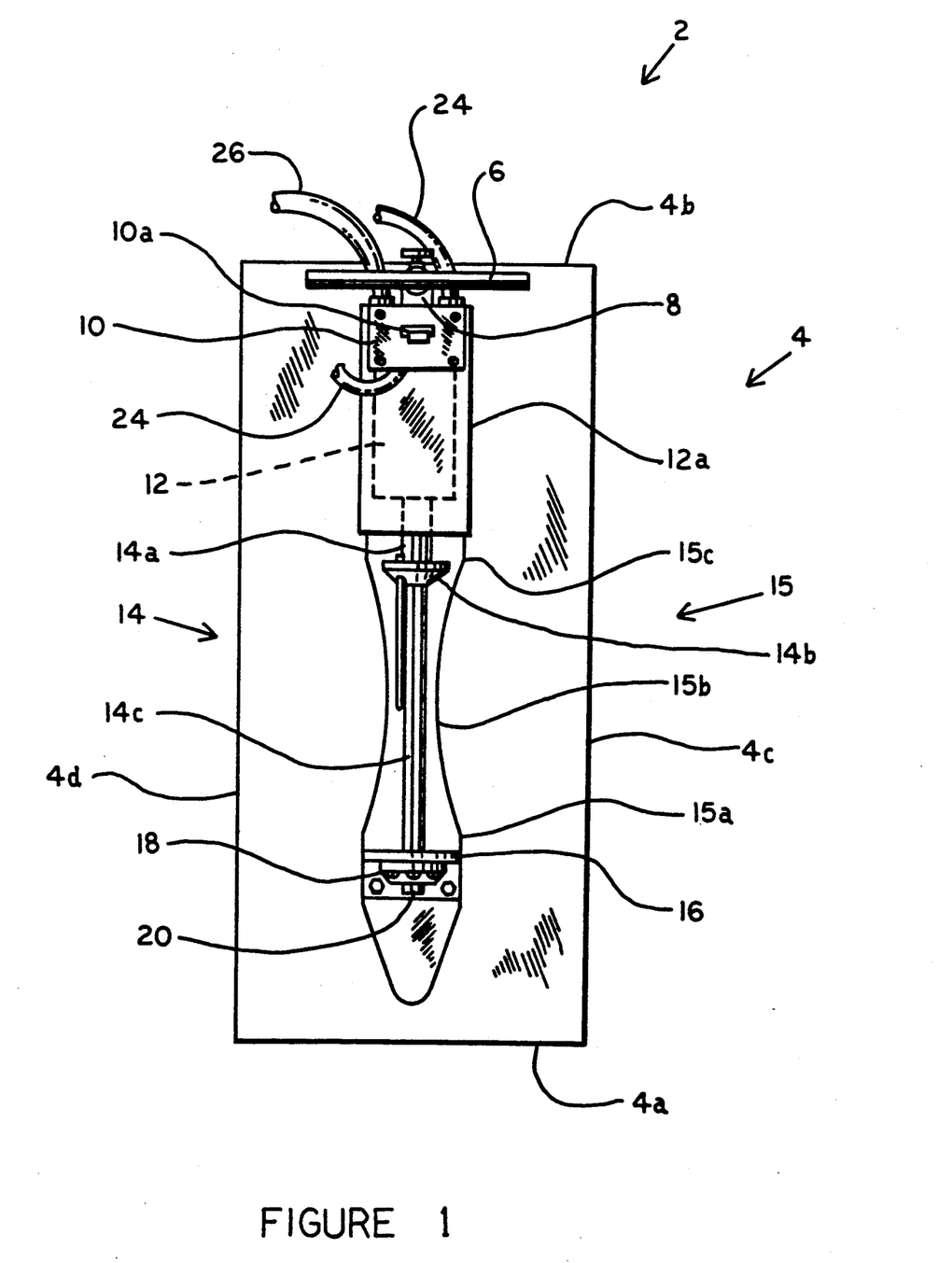
FIG. 1 is a top plan view of a first embodiment of a prosthetic machine made in accordance with the principles of the present invention.
Figure 2:
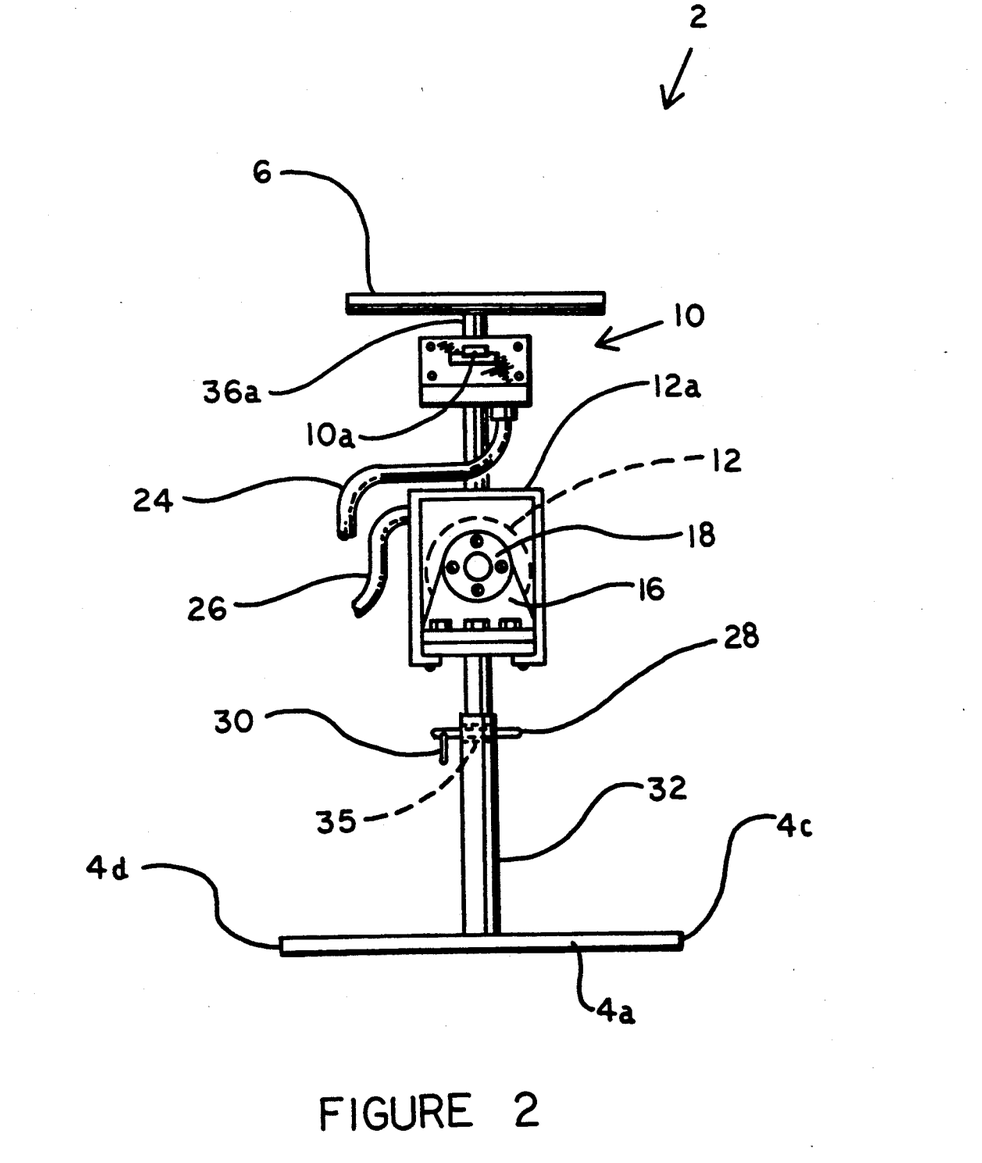
FIG. 2 is a frontal view of the machine shown in FIG. 1.
Figure 3:
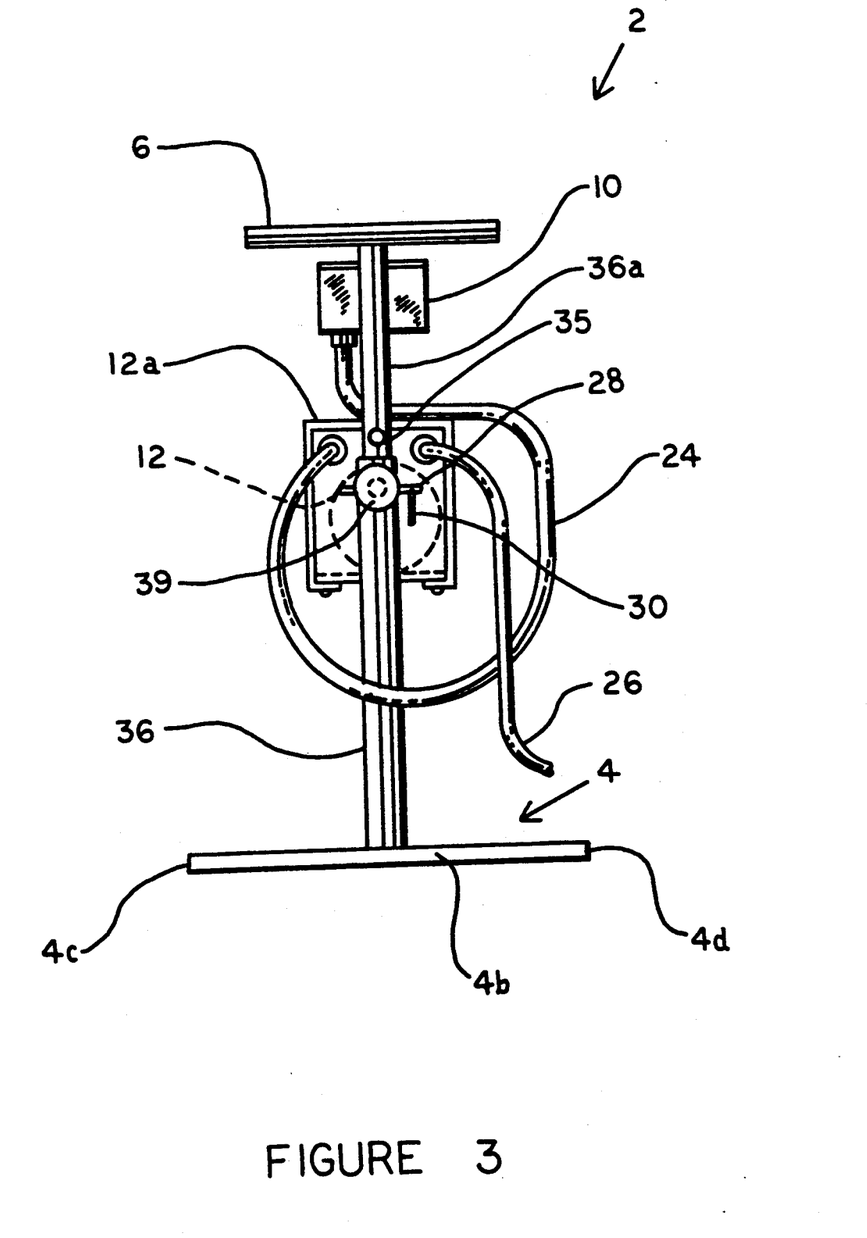
FIG. 3 is a rearward view of the machine shown in FIG. 1.
Figure 4:
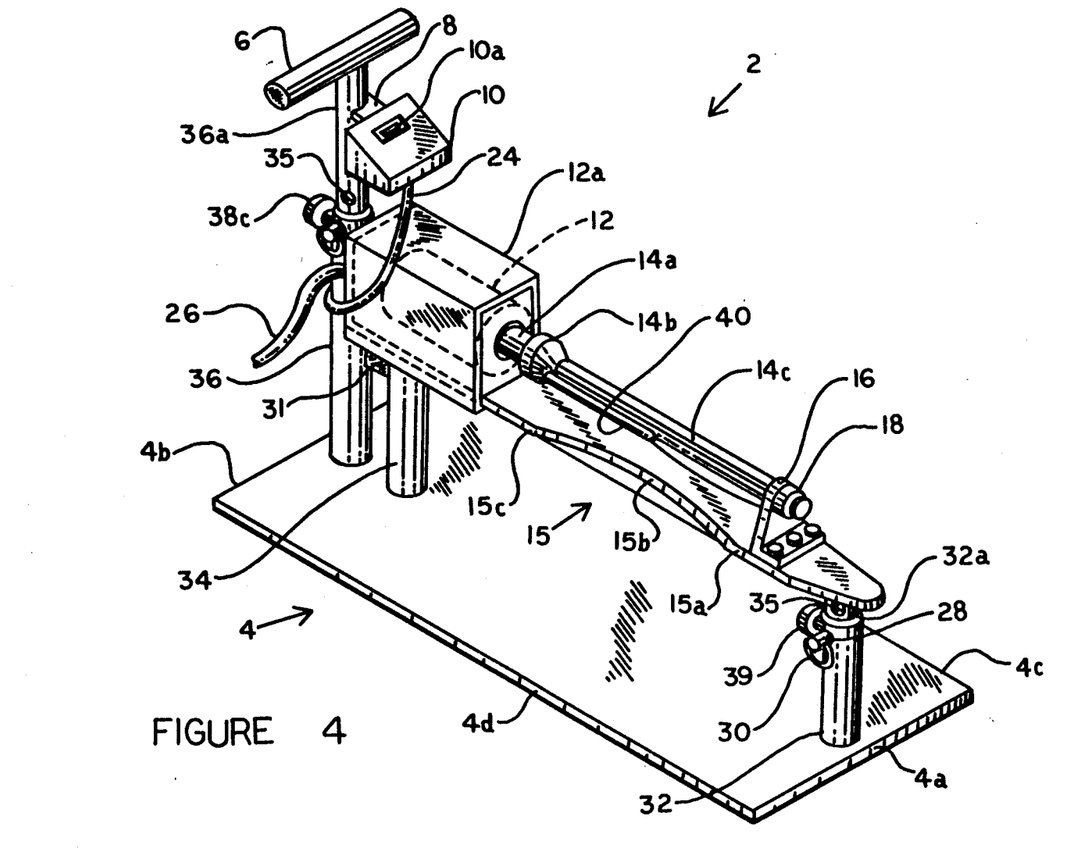
FIG. 4 is an isometric view of the machine shown in FIG. 1.
Figure 5:
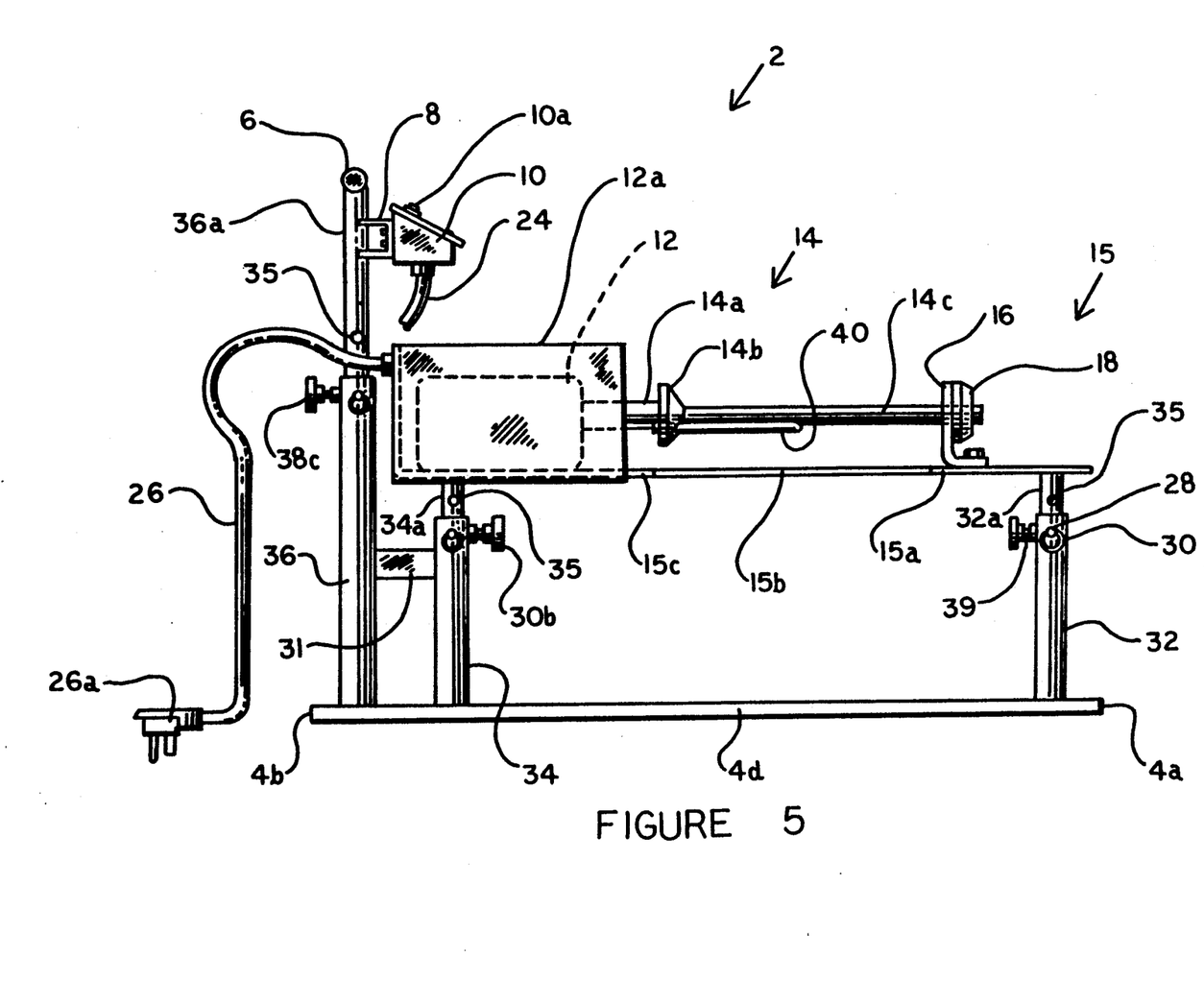
FIG. 5 is a view of the machine shown in FIG. 1, taken from the left-hand side of the machine.
Figure 8:
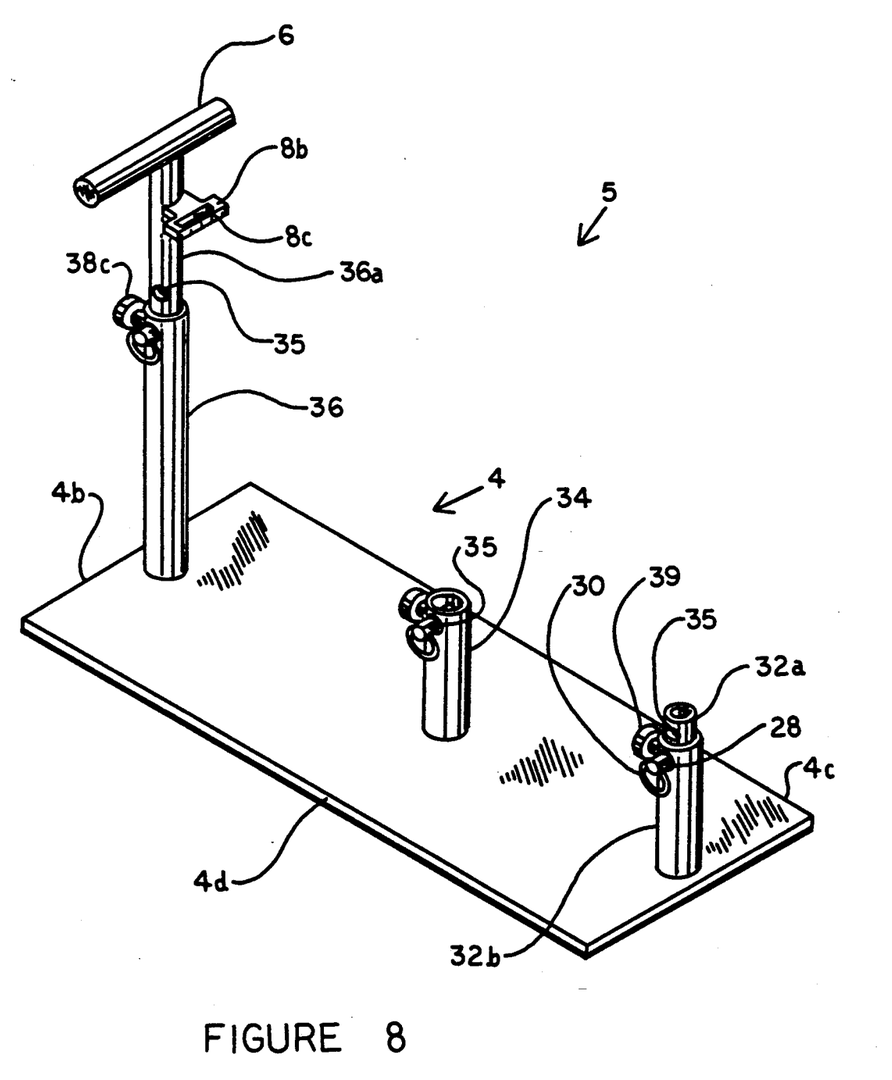
FIG. 8 is an isometric view of a frame for the machine shown in FIG. 7.

The frame 5 comprises the horizontal base 4; the support members 36, 36a, 34, 32a, and 32b; and the handlebar 6 of the machine 2 shown in FIG. 4. Attached to the movable support member 36a is a horizontal plate 8b having a slit 8c for disposal therein of the vertical portion 9b of the L-shaped member 9, for attaching the control panel 10 to the movable support member 36a.

After the base 5 and stationary support member 34 have been detached from the machine 3, the remaining parts of the machine 3 are mounted on the frame 5 by (a) attaching the panel 10 to support member 36a, (b) disposing the movable support member 34a in the stationary support member 34 fastened to the base 4, and (c) fitting the stationary support member 33 over the movable support member 32a, which then supports the stationary support member 33.

I claim:

1. A machine for attaching a prosthesis to an above-the knee amputee, comprising:
   (a) a frame including a horizontal base;
   (b) a motor mounted on the frame;
   ($c_1$) means for switching the motor on and off, and
   ($c_2$) means for varying the vertical distance from the motor to the base of the frame;
   (d) a rigid, elongated, horizontal member having first and second ends, the first end of the elongated member being rotatably connected to the motor; and
   (e) means for holding a tubular stocking in contact with the elongated member, the stocking having first and second ends, the first end of the stocking being held in contact with the elongated member, the elongated member and the holding means being so constructed and arranged that, as the elongated member is turned by the motor, the tubular stocking is wrapped around the elongated member, thereby drawing the second end of the stocking toward the elongated member.

2. A machine for attaching a prosthesis to an above-the-knee amputee, comprising:
   (a) a frame including
      ($a_1$) a horizontal base;
      ($a_2$) first, second, and third vertically-adjustable support members fastened to the base;
      ($a_3$) a horizontal plate supported by the first and second support members; and
      ($a_4$) a vertical plate supported by the horizontal plate;
   (b) a motor mounted on the frame;
   ($c_1$) means for switching the motor on and off, and
   ($c_2$) means for varying the vertical distance from the motor to the base of the frame;

(d) a rigid, elongated, horizontal member having first and second ends, the first end of the elongated member being rotatably connected to the motor; and (e) means for holding a tubular stocking in contact with the elongated member, the stocking having first and second ends, the first end of the stocking being held in contact with the elongated member, the elongated member and the holding means being so constructed and arranged that, as the elongated member is turned by the motor, the tubular stocking is wrapped around the elongated member, thereby drawing the second end of the stocking toward the elongated member;

the horizontal plate providing support for the motor and the elongated horizontal member, the vertical plate including an opening therein for passage therethrough of the second end of the elongated horizontal member, the vertical plate having a first surface facing the motor and a second surface facing away from the motor.

3. The machine of claim 2, wherein the second end of the elongated member is disposed in a bearing attached to the surface of the vertical plate facing away from the motor, the vertical plate and the bearing being constructed and arranged so that the second end of the elongated member passes through the opening in the plate and is disposed in the bearing.

4. The machine of claim 2, further comprising:
(f) holding means connected to the upper end of the third support member, to serve as a handle for the amputee.

5. The machine of claim 1, wherein:
($b_1$) the motor is a reversible electric gear motor; and
($c_1$) the switching means include a momentary switch which can be started and stopped at any time.

6. A machine for attaching a prosthesis to an above-the-knee amputee, comprising:
(a) a frame including
($a_1$) a horizontal base;
($a_2$) a vertically-adjustable first support member comprising a stationary vertical member, fastened to the base, and a movable vertical member disposed within the stationary vertical member;
($a_3$) a second support member fastened to the base;
($a_4$) a horizontal plate supported by the first and second support members; and
($a_5$) a vertical plate supported by the horizontal plate;
(b) a motor mounted on the frame;
($c_1$) means for switching the motor on and off, and
($c_2$) means for varying the vertical distance from the motor to the base of the frame;
(d) a rigid, elongated, horizontal member having first and second ends, the first end of the elongated member being rotatably connected to the motor; and
(e) means for holding a tubular stocking in contact with the elongated member, the stocking having first and second ends, the first end of the stocking being held in contact with the elongated member, the elongated member and the holding means being so constructed and arranged that, as the elongated member is turned by the motor, the tubular stocking is wrapped around the elongated member, thereby drawing the second end of the stocking toward the elongated member;
the horizontal plate providing support for the motor and the elongated horizontal member, the vertical plate including an opening therein for passage therethrough of the second end of the elongated horizontal member, the vertical plate having a first surface facing the motor and a second surface facing away from the motor.

7. The machine of claim 6, wherein the second end of the elongated member is disposed in a bearing attached attached to the surface of the vertical plate facing away from the motor, the vertical plate and the bearing being constructed and arranged so that the second end of the elongated member passes through the opening in the plate and is disposed in the bearing.

8. The machine of claim 1, further comprising:
(f) a control panel which includes the switch means for the motor; and
(g) a horizontal bar, which serves as a handle, connected to the control panel.

9. The machine of claim 6, wherein the frame further includes:
($a_6$) a second horizontal base;
($a_7$) a vertically-adjustable third support member fastened to the second base;
($a_8$) a fourth support member fastened to the second base, the fourth support member and the movable vertical member of the first support member being so constructed and arranged that the movable support member of the first support member is disposable within the fourth support member;
($a_9$) a vertically-adjustable fifth support member comprising a stationary vertical member, fastened to the second base, and a movable vertical member disposed within the stationary vertical member, the second and fifth support members being so constructed and arranged that the movable vertical member of the fifth support member is disposable within the second support member; and
($a_{10}$) means for attaching the control panel to the third support member;
the first, second, third, fourth, and fifth support members being so constructed and arranged that the first base and the stationary member of the first support member can be detached from the remaining portion of the machine, and the remaining portion of the machine can be fixed to the second base by disposing the movable member of the first support member within the third support member, and by disposing the movable member of the fifth support member within the second support member, thereby transforming the machine from a portable machine to a fixed machine.

10. The machine of claim 1, wherein the speed of the motor is 8.8 revolutions per minute.

11. The machine of claim 2, wherein the horizontal plate includes a recessed, concave portion between the first and second ends of the plate.

12. The machine of claim 2, wherein the horizontal plate includes a recessed, concave portion which effectively braces the prosthesis and thereby prevents the prosthesis from buckling at the knee.

13. The machine of claim 2, wherein the height of the horizontal member is from about fourteen to about twenty-eight inches above the horizontal base.

14. The machine of claim 6, wherein the horizontal plate includes a recessed, concave portion between the first and second ends of the plate.

15. The machine of claim 6, wherein the horizontal plate includes a recessed, concave portion which effectively braces the prosthesis and thereby prevents the prosthesis from buckling at the knee.

16. The machine of claim 6, wherein the height of the elongated horizontal member is from about fourteen to about twenty-eight inches above the horizontal base.

17. The machine of claim 1, wherein the means for varying the distance from the motor to the base of the frame are internal means integral with the frame.

* * * * *